(12) United States Patent
Rosario-Melendez et al.

(10) Patent No.: US 10,786,439 B2
(45) Date of Patent: Sep. 29, 2020

(54) SATIN LIP COMPOSITIONS

(71) Applicant: L'ORÉAL, Paris (FR)

(72) Inventors: Roselin Rosario-Melendez, New York, NY (US); Tianyi Liu, Springfield, PA (US)

(73) Assignee: L'ORÉAL, Paris (FR)

( * ) Notice: Subject to any disclaimer, the term of this patent is extended or adjusted under 35 U.S.C. 154(b) by 113 days.

(21) Appl. No.: 16/023,982

(22) Filed: Jun. 29, 2018

(65) Prior Publication Data

US 2020/0000702 A1 Jan. 2, 2020

(51) Int. Cl.
*A61Q 1/06* (2006.01)
*A61K 8/81* (2006.01)
*A61K 8/36* (2006.01)
*A61K 8/89* (2006.01)

(52) U.S. Cl.
CPC .............. *A61K 8/8141* (2013.01); *A61K 8/36* (2013.01); *A61K 8/8111* (2013.01); *A61K 8/89* (2013.01); *A61Q 1/06* (2013.01); *A61K 2800/26* (2013.01); *A61K 2800/31* (2013.01); *A61K 2800/34* (2013.01)

(58) Field of Classification Search
CPC .................................... A61K 8/89; A61Q 1/06
See application file for complete search history.

(56) References Cited

U.S. PATENT DOCUMENTS

| | | | | |
|---|---|---|---|---|
| 7,482,419 B2 * | 1/2009 | Caprasse | ................. | A61K 8/06 528/15 |
| 9,789,055 B2 * | 10/2017 | Bui | ......................... | A61Q 1/06 |
| 10,272,027 B2 * | 4/2019 | Bui | ........................ | A61K 8/895 |
| 2009/0004132 A1 | 1/2009 | Nicholson et al. | | |
| 2012/0014899 A1 * | 1/2012 | Dop | ........................ | A61K 8/06 424/70.121 |
| 2015/0366779 A1 * | 12/2015 | Bui | ........................ | A61Q 1/06 424/64 |
| 2015/0366780 A1 * | 12/2015 | Bui | ........................ | A61K 8/895 424/64 |
| 2015/0366782 A1 | 12/2015 | Bui et al. | | |

FOREIGN PATENT DOCUMENTS

WO  WO 2015/193413 A1  12/2015

OTHER PUBLICATIONS

International Search Report and Written Opinion dated Oct. 8, 2019, in PCT/US2019/039409, 13 pages.

* cited by examiner

*Primary Examiner* — Margaret G Moore
(74) *Attorney, Agent, or Firm* — Oblon, McClelland, Maier & Neustadt, L.L.P.

(57) ABSTRACT

The present invention relates to satin lip compositions including at least one silicone resin comprising at least one T unit, at least one silicone acrylate copolymer, at least one silicone wax, at least one volatile hydrocarbon oil, and at least one non-volatile hydrocarbon oil having a molecular weight greater than 400 g/mol, as well as to methods of making such compositions and methods of applying such compositions to lips.

20 Claims, No Drawings

SATIN LIP COMPOSITIONS

FIELD OF THE INVENTION

The present invention relates to satin lip compositions comprising at least one silicone resin comprising at least one T unit, at least one silicone acrylate copolymer, at least one silicone wax, at least one volatile hydrocarbon oil, and at least one non-volatile hydrocarbon oil, as well as to methods of making such compositions and methods of applying such compositions to lips.

DISCUSSION OF THE BACKGROUND

Many cosmetic compositions, including pigmented cosmetics such as lipsticks or lip colors, have been formulated in an attempt to possess long-wearing properties upon application. Unfortunately, many of these compositions do not generally possess good long-wear/transfer-resistance properties as well as good appearance properties (for example, satin properties) and/or application properties.

With respect to lip compositions, commercial products containing silicon resins such as MQ resins are known. Such products are known to provide good long wear properties/transfer-resistance. However, such products possess poor application properties and/or poor feel upon application (for example, feels rough).

Typically, a second composition (topcoat) is separately applied to such products to improve poor properties of the compositions to make the products acceptable to consumers. However, topcoat compositions tend to decrease the long-wear/transfer-resistance properties of the lip compositions, thereby rendering the long-wear/transfer resistant composition less acceptable to consumers and less acceptable for their intended purpose.

Thus, there remains a need for improved satin lip compositions having improved cosmetic properties, particularly good transfer-resistance, feel and/or satin characteristics upon application.

SUMMARY OF THE INVENTION

The present invention relates to satin lip compositions comprising at least one silicone resin comprising at least one T unit, at least one silicone acrylate copolymer, at least one silicone wax, at least one volatile hydrocarbon oil, and at least one non-volatile hydrocarbon oil. Preferably, the composition further comprises at least one colorant.

The present invention also relates to satin lip compositions comprising about 10% to about 40% by weight of at least one silicone resin comprising at least one T unit, about 5% to about 40% by weight of at least one silicone acrylate copolymer, about 1% to about 15% by weight of at least one silicone wax, about 1% to about 15% by weight of at least one volatile hydrocarbon oil, and about 1% to about 30% at least one non-volatile hydrocarbon oil, all weights being based on the total weight of the composition. Preferably, the composition further comprises at least one colorant.

The present invention also relates to methods of making a satin lip composition comprising combining at least one silicone resin comprising at least one T unit, at least one silicone acrylate copolymer, at least one silicone wax, at least one volatile hydrocarbon oil, and at least one non-volatile hydrocarbon oil, during preparation of the composition to form a satin lip composition. Preferably, at least one colorant is also added during preparation of the composition.

The present invention also relates to methods of making a satin lip composition comprising combining about 10% to about 40% by weight of at least one silicone resin comprising at least one T unit, about 5% to about 40% by weight of at least one silicone acrylate copolymer, about 1% to about 15% by weight of at least one silicone wax, about 1% to about 15% by weight of at least one volatile hydrocarbon oil, and about 1% to about 30% at least one non-volatile hydrocarbon oil, all weights being based on the total weight of the composition, during preparation of the composition to form a satin lip composition. Preferably, at least one colorant is also added during preparation of the composition.

The present invention further relates to methods for making up and/or protecting lips comprising applying to the lips a satin lip composition comprising at least one silicone resin comprising at least one T unit, at least one silicone acrylate copolymer, at least one silicone wax, at least one volatile hydrocarbon oil, and at least one non-volatile hydrocarbon oil. Preferably, the composition further comprises at least one colorant.

The present invention further relates to methods for making up and/or protecting lips comprising applying to the lips a satin lip composition comprising about 10% to about 40% by weight of at least one silicone resin comprising at least one T unit, about 5% to about 40% by weight of at least one silicone acrylate copolymer, about 1% to about 15% by weight of at least one silicone wax, about 1% to about 15% by weight of at least one volatile hydrocarbon oil, and about 1% to about 30% at least one non-volatile hydrocarbon oil, all weights being based on the total weight of the composition. Preferably, the composition further comprises at least one colorant.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual ingredients or components as well as mixtures/combinations of ingredients or components.

Other than in the operating examples, or where otherwise indicated, all numbers expressing quantities of ingredients and/or reaction conditions are to be understood as being modified in all instances by the term "about," meaning within 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to lips and evaluating the color of the composition after an extended period of time. For example, the color of a composition may be evaluated immediately following application to lips and these characteristics may then be re-evaluated and compared after a certain amount of time.

Further, these characteristics may be evaluated with respect to other compositions, such as commercially available compositions.

Anhydrous refers to a composition not containing any water, that is to say a composition in which the water that may be present comes only from the water of crystallization or of adsorption of the starting materials. In any case, an "anhydrous composition" in accordance with the present invention contains less than 3% by weight of water, preferably less than 1% by weight, and better still less than 0.5% by weight of water, relative to the total weight of the composition. A composition of the present invention may also contain no water.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions. For lip compositions, "long wear" typically means the composition remains on the lips at least about 4 hours up to about 24 hours, and retains rich color even after eating.

"Liquid" or "liquid cosmetic" or "liquid lipstick" or "liquid composition" means a composition having a fixed volume, flows to cover the bottom and assumes the shape of the portion of the container it fills and is slightly compressible (as disclosed in *General chemistry*, Fourth Edition 2005, p. 434).

"Adhesion" as used herein, refers to chemical or physical bonding between a coating and a substrate. Good adhesion between a lip composition and lips should translate to good wear properties on consumers. Adhesion properties can be quantified by in-vitro method such as a cross-cut adhesion test. In the test, a lattice pattern is cut into the coating and penetrates through to the substrate. A pressure sensitive tape is applied to the sample and then pulled off. The adhesion property can be quantified by the area of the coating remaining after peeling. For example, if the whole film remains after peeling, it indicates excellent adhesion. If most of the film gets peeled off, it indicates poor adhesion. The cross-cut test is an industrial standard test for testing adhesion for coatings. (Reference # ISO/DIN 2409, ASTM D3359).

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Satin" in compositions as used herein refers to compositions having little light reflection. For example, satin compositions can have average gloss properties, measured at 60°, of greater than or equal to 20, preferably greater than or equal to 25, preferably greater than or equal to 29, and preferably greater than or equal to 30, and less than or equal to 60, preferably less than or equal to 50, preferably less than or equal to 40, and preferably less than or equal to 35, including all ranges and subranges therebetween such as, for example, 20-60, 29-40, and 25-35, etc.

"Free" or "substantially free" or "devoid of" as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. Thus, for example, "free of silicone gum" means that silicone gums are omitted from the composition (that is, 0% by weight), "substantially free of silicone gum" means that silicone gums are present in amounts not greater than 0.1% by weight, and "devoid of silicone gum" means that silicone gums are present in amounts not greater than 0.25% by weight, based on the total weight of the composition. The same nomenclature applies for other ingredients such as, for example, silicone oils ("free of silicone oils," "substantially free of silicone oils," and "devoid of silicone oils" have meanings consistent with the discussion within this paragraph).

The compositions and methods of the present invention can "comprise," "consist of" or "consist essentially of" the essential elements and limitations of the invention described herein, as well as any additional or optional ingredients, components, or limitations described herein or otherwise useful. For purposes of the compositions and methods of the present invention where the invention "consists essentially of" the identified ingredients and/or process steps, the sole "basic and novel property" of such compositions and/or methods is "satin" appearance. As an example, it has been found that high levels of magnesium stearate can have a material adverse effect on the satin appearance of compositions of the present invention. The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

Satin Lip Composition

According to the present invention, satin lip compositions comprising at least one silicone resin comprising at least one T unit, at least one silicone acrylate copolymer, at least one wax, at least one volatile hydrocarbon oil, and at least one non-volatile hydrocarbon oil are provided.

Silicone Resin Comprising at Least One T Unit

According to the present invention, compositions comprising at least one silicon resin comprising at least one T unit are provided. Suitable silicone resins in accordance with the present invention are disclosed, for example, in U.S. patent applications 2007/0166271, 2011/0038820, 2011/0002869, and 2009/0214458, the entire contents of which are hereby incorporated by reference in their entirety.

As used herein, the term "resin" means a crosslinked or non-crosslinked three-dimensional structure. Examples of polysiloxane T resins that may be mentioned include silsesquioxanes and siloxysilicates.

The nomenclature of silicone resins is known under the name MDTQ, the resin being described as a function of the various siloxane monomer units it comprises, each of the letters MDTQ characterizing a type of unit.

The letter M represents the monofunctional unit, for example, of formula $(CH_3)_3SiO_{1/2}$, the silicon atom being connected to only one oxygen atom in the polymer comprising this unit.

The letter D means a difunctional unit, for example, $(CH_3)_2SiO_{2/2}$ in which the silicon atom is connected to two oxygen atoms.

The letter T represents a trifunctional unit, for example, of formula $(CH_3)SiO_{3/2}$.

In the M, D and T units listed as examples above, at least one of the methyl groups may be substituted. In some embodiments, the at least one silicone resin comprising at least one trifunctional unit of formula $(R)SiO_{3/2}$ is chosen from the silsesquioxanes of formula: $((R')SiO_{3/2})_x$, in which x ranges from 100 to 500 and R' is chosen, independently by trifunctional unit, from a hydrocarbon-based group containing from 1 to 10 carbon atoms or a hydroxyl group, on the condition that at least one R' is a hydrocarbon-based group. In some embodiments, the hydrocarbon-based group containing from 1 to 10 carbon atoms is a methyl group. In some embodiments, the at least one silicone resin comprising at least one trifunctional unit of formula $(R)SiO_{3/2}$ is chosen from the silsesquioxanes of the formula: $((R')SiO_{3/2})_x$, in which x ranges from 100 to 500 and R' is chosen, independently by unit, from $CH_3$, a hydrocarbon-based group containing from 2 to 10 carbon atoms, or a hydroxyl group, on the condition that at least one R' is a hydrocarbon-based group.

Finally, the letter Q means a tetrafunctional unit $SiO_{4/2}$ in which the silicon atom is bonded to four hydrogen atoms, which are themselves bonded to the rest of the polymer.

Various resins with different properties may be obtained from these different units, the properties of these polymers varying as a function of the type of monomers (or units), of the type and number of substituted groups, of the length of the polymer chain, of the degree of branching and of the size of the side chains.

The silicone resin contains at least one T unit. It may thus be, for example, a T, MT, MTQ or MDTQ resin.

In some embodiments, the unit composition of the silicone resin is at least 50% T units, or at least 70% T units, or at least 80% T units, or at least 90% T units.

In some embodiments, the T resins may contain M, D and Q units such that at least 80 mol % or at least 90 mol %, relative to the total amount of silicones, are T units. The T resins may also contain hydroxyl and/or alkoxy groups. The T resins may have a total weight of hydroxyl functions ranging from 2% to 10% and a total weight of alkoxy functions that may be up to 20%; in some embodiments, the total weight of hydroxyl functions ranges from 4% to 8% and the total weight of alkoxy functions may be up to 10%.

The silicone resin may be chosen from silsesquioxanes that are represented by the following formula: $((CH_3)SiO_{3/2})_x$, in which x may be up to several thousand and the $CH_3$ group may be replaced with an R group, as described previously in the definition of the T units. The number x of T units of the silsesquioxane may be less than or equal to 500, or it may range from 50 to 500, including all ranges and subranges therebetween. The molecular weight of the silicone resin may range from 500 to 50,000 g/mol, from 500 to 20,000 g/mol, or from 500 to 10,000 g/mol, including all ranges and subranges therebetween.

The silicone resin may be film-forming. Specifically, not all silsesquioxanes are film-forming: for example, highly polymerized polymethylsilsesquioxanes such as Tospearl™ from Toshiba or KMP590 from Shin-Etsu are insoluble and are not film-forming. The molecular weight of these polymethylsilsesquioxanes is difficult to determine, but there are generally more than 1000 T units.

As suitable examples of these silicone resins containing at least one T unit, mention may be made of:

polysilsesquioxanes of formula $((R)SiO_{3/2})_x$ (T units) in which x is greater than 100, in which the R groups may independently be methyl or other substituents as defined above;

polymethylsilsesquioxanes, which are polysilsesquioxanes in which R is a methyl group. Such polymethylsilsesquioxanes are described, for example, in U.S. Pat. No. 5,246,694, the entire contents of which is hereby incorporated by reference in its entirety;

polypropylsilsesquioxanes, in which R is a propyl group. These compounds and their synthesis are described, for example, in patent application WO 2005/075567, the entire contents of which is hereby incorporated by reference in its entirety;

polyphenylsilsesquioxanes, in which R is a phenyl group. These compounds and their synthesis are described, for example, in patent application US 2004/0180011, the entire contents of which is hereby incorporated by reference in its entirety.

Examples of commercially available polymethylsilsesquioxane resins that may be mentioned include those sold:

by the company Wacker under the reference Resin MK such as Belsil PMS MK: polymer comprising $CH_3SiO_{3/2}$ repeating units (T units), which may also comprise up to 1% by weight of $(CH_3)_2SiO_{2/2}$ units (D units) and having an average molecular weight of about 10 000 g/mol. It is thought that the polymer is in a "cage" and "ladder" configuration as represented in the FIGURES below. The average molecular weight of the units in "cage" configuration has been calculated as 536 g/mol. The majority of the polymer is in the "ladder" configuration with ethoxy groups at the ends. These ethoxy groups represent 4.5% by mass of the polymer. As these end groups can react with water, a small and variable amount of SiOH groups may also be present;

by the company Shin-Etsu under the references KR-220L, which are composed of T units of formula $CH_3SiO_{3/2}$ and have Si—OH (silanol) end groups, under the reference KR-242A, which comprise 98% of T units and 2% of dimethyl D units and have Si—OH end groups or alternatively under the reference KR-251 comprising 88% of T units and 12% of dimethyl D units and have Si—OH end groups.

Examples of commercially available polypropylsilsesquioxane resins that may be mentioned include those sold:

by the company Dow Corning under the reference Dow Corning 670 Fluid, which is a polypropylsilsesquioxane diluted in volatile oil such as volatile hydrocarbon oil or volatile silicone oil such as D5.

Examples of commercially available polyphenylsilsesquioxane resins that may be mentioned include those sold:

by the company Dow Corning under the reference Dow Corning 217 Flake Resin, which is a polyphenylsilsesquioxane with silanol end groups;

by the company Wacker under the reference Belsil SPR 45 VP.

The at least one silicone resin comprising at least one T unit is preferably present in the satin lip compositions of the present invention in an amount ranging from about 10% to about 40% by weight, preferably from about 15% to about 35% by weight, and preferably from about 17% to about 32% by weight, including all ranges and subranges therebetween, all weights being based on the weight of the composition as a whole.

Silicone Acrylate Copolymer

In accordance with the present invention, satin lip compositions comprising at least one silicone acrylate copolymer are provided.

Suitable silicone acrylate copolymers include polymers comprising a siloxane group and a hydrocarbon group. In some embodiments, such silicone acrylate copolymers comprise at least about 10%, 20%, 30%, 40%, 50%, 60%, 70%, 80%, or 90% silicone by weight. For example, suitable polymers include polymers comprising a hydrocarbon backbone such as, for example, a backbone chosen from vinyl polymers, methacrylic polymers, and/or acrylic polymers and at least one chain chosen from pendant siloxane groups, and polymers comprising a backbone of siloxane groups and at least one pendant hydrocarbon chain such as, for example, a pendant vinyl, methacrylic and/or acrylic groups.

The at least one silicone acrylate copolymer can be chosen from silicone/(meth)acrylate copolymers, such as those as described in U.S. Pat. Nos. 5,061,481, 5,219,560, and 5,262,087, and U.S. patent application 2012/0301415, the entire contents of all of which are hereby incorporated by reference.

The at least one silicone acrylate copolymer may be selected from polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (INCI name: isododecane (and) acrylate/dimethicone copolymer), KP-561 (acrylates/stearyl acrylate/dimethicone acrylates copolymer), KP-562 (acrylates/behenyl acrylate/dimethicone acrylates copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Further non-limiting examples of such polymers and their synthesis are disclosed, for example, in U.S. Pat. Nos. 4,972,037, 5,061,481, 5,209,924, 5,849,275, and 6,033,650, and PCT applications WO 93/23446 and WO 95/06078, the disclosures of all of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Other non-limiting examples of useful silicone acrylate copolymers include silicone/acrylate graft terpolymers, for example, the copolymers described in PCT application WO 01/32727, the disclosure of which is hereby incorporated by reference.

Other useful polymers include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

Suitable silicone acrylate copolymers include silicone/(meth)acrylate copolymers, such as those as described in U.S. Pat. Nos. 5,219,560, and 5,262,087, the disclosures of which are hereby incorporated by reference. Still further non-limiting examples of silicone film formers are non-polar silicone copolymers comprising repeating units of at least one polar (meth)acrylate unit and vinyl copolymers grafted with at least one non-polar silicone chain.

Other non-limiting examples of silicone film formers suitable for use in the present invention are silicone esters comprising units of formulae (A) and (B), disclosed in U.S. Pat. Nos. 6,045,782, 5,334,737, and 4,725,658, the disclosures of which are hereby incorporated by reference:

$$R_a R^E_b SiO_{[4-(a+b)/2]} \quad (A); \text{ and}$$

$$R'_x R^E_y SiO_{1/2} \quad (B)$$

wherein

R and R', which may be identical or different, are each chosen from optionally substituted hydrocarbon groups;

a and b, which may be identical or different, are each a number ranging from 0 to 3, with the proviso that the sum of a and b is a number ranging from 1 to 3, x and y, which may be identical or different, are each a number ranging from 0 to 3, with the proviso that the sum of x and y is a number ranging from 1 to 3;

$R^E$, which may be identical or different, are each chosen from groups comprising at least one carboxylic ester.

According to preferred embodiments, $R^E$ groups are chosen from groups comprising at least one ester group formed from the reaction of at least one acid and at least one alcohol. According to preferred embodiments, the at least one acid comprises at least two carbon atoms. According to preferred embodiments, the at least one alcohol comprises at least ten carbon atoms. Non-limiting examples of the at least one acid include branched acids such as isostearic acid, and linear acids such as behenic acid. Non-limiting examples of the at least one alcohol include monohydric alcohols and polyhydric alcohols, such as n-propanol and branched etheralkanols such as (3,3,3-trimethylolpropoxy)propane.

Further non-limiting examples of the at least one silicone acrylate copolymer film former include liquid siloxy silicates and silicone esters such as diisostearoyl trimethylolpropane siloxysilicate and dilauroyl trimethylolpropane siloxy silicate, which are commercially available from General Electric under the tradenames SF 1318 and SF 1312, respectively.

The at least one silicone acrylate copolymer is preferably present in satin lip compositions of the present invention in an amount ranging from about 5% to about 40% by weight, preferably from about 7% to about 30% by weight, and preferably from about 8% to about 20% by weight, including all ranges and subranges therebetween, all weights being based on the weight of the composition as a whole.

According to preferred embodiments, the silicone resin(s) comprising at least one T unit and silicone acrylate copolymer(s) are present in the satin lip compositions of the present invention in a preferred weight ratio of from about 5:1 to about 1:5, preferably from about 4:1 to about 1:4, preferably from about 3:1 to about 1:3, including all ranges and subranges therebetween such as, for example, about 3:1 to about 1:1, about 3:1 to about 1.5:1, 4:1 to about 2:1, etc.

The at least one silicone acrylate copolymer and the at least one silicone resin comprising at least one T unit are preferably present in the satin lip compositions of the present invention in a combined amount ranging from about 20% to about 80% by weight, preferably from about 25% to about 70% by weight, and preferably from about 30% to about 50% by weight, including all ranges and subranges therebetween, all weights being based on the weight of the composition as a whole.

Silicone Wax

In accordance with the present invention, satin lip compositions comprising at least one silicone wax are provided. Preferably, the wax is a lipophilic fatty compound that is solid at room temperature (25° C.), has a reversible solid/liquid change of state (that is, the state of the material may change based on temperature), has a melting point greater than 45° C., preferably greater than 55° C., more preferably between about 65° C. to about 120° C., and has anisotropic crystal organization in the solid state. The melting point of the wax may be measured using a differential scanning calorimeter (DSC), for example the calorimeter sold under the name DSC 30 by Mettler.

Preferably, the at least one silicone wax is a polypropylsilsesquioxane wax substituted with alkyl units having at least 30 carbons. Polypropylsilsesquioxane waxes, in general, have been disclosed in patent publication WO2005/100444, the entire contents of which is hereby incorporated by reference.

Preferably, the polypropylsilsesquioxane wax comprises at least 40 mole % of siloxy units having the formula $(R_2R'SiO_{1/2})_x(C_3H_7SiO_{3/2})_y$, where x and y have a value of 0.05 to 0.95, R is an alkyl group having from 1 to 8 carbon atoms, and R' is a monovalent hydrocarbon having 30 to 40 carbon atoms or greater. As used herein, x and y represent the mole fraction of $(R_2R'SiO_{1/2})$ and $(C_3H_7SiO_{3/2})$ siloxy units relative to each other present in the polypropylsilsesquioxane wax. Thus, the mole fraction of $(R_2R'SiO_{1/2})$ and $(C_3H_7SiO_{3/2})$ siloxy units each can independently vary from 0.05 to 0.95. Preferably R is a methyl, and R' is an alkyl having at least 30 carbons, available from Dow Corning.

Preferably, value of x is 0.05 to 0.95, or preferably, 0.2 to 0.8, and the value of y is 0.05 to 0.95, preferably 0.2 to 0.8. However, the combination of $(R_2R'SiO_{1/2})$ and $(C_3H_7SiO_{3/2})$ siloxy units present must total at least 40 mole %, preferably 60 mole %, and preferably 90 mole % of all siloxy units present in the polypropylsilsesquioxane wax.

Preferably, the number average molecular weight of the polypropylsilsesquioxane wax substituted with alkyl units having at least 30 carbons typically ranges from about 750 to about 10,000, preferably from about 1,000 to about 5,000, including all ranges and subranges therebetween.

A particularly preferred polypropylsilsesquioxane wax for use in the present invention is a C30-45 ALKYLDIMETHYLSILYL POLYPROPYLSILSESQUIOXANE commercially available from DOW CORNING under the tradename SW-8005 C30 Resin Wax. Preferably, silicone wax is present in the satin lip compositions of the present invention in an amount ranging from about 1% to about 15% by weight, preferably from about 1.5% to about 12.5% by weight, and preferably from about 2% to about 10% by weight, including all ranges and subranges therebetween, all weights based on the weight of the composition as a whole.

Volatile Hydrocarbon Oil

In accordance with the present invention, satin lip compositions comprising at least one volatile hydrocarbon oil are provided. Examples of suitable volatile hydrocarbon oils include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
|---|---|
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Preferably, the volatile hydrocarbon oil is present in the satin lip compositions of the present invention in amounts ranging from about 1% to about 30%, preferably from about 2% to about 25% and preferably from about 5% to about 20%, by weight, based on the total weight of the composition, including all ranges and subranges in between.

Non-Volatile Hydrocarbon Oil Having A Molecular Weight Greater Than 400 g/mol

In accordance with the present invention, satin lip compositions comprising at least one non-volatile hydrocarbon oil having a molecular weight greater than 400 g/mol are provided.

According to preferred embodiments, the non-volatile hydrocarbon oil is apolar and/or is chosen from linear or branched hydrocarbons of mineral or synthetic origin.

Preferably, the at least one non-volatile hydrocarbon oil having a molecular weight greater than 500 g/mol, preferably greater than 700 g/mol, preferably greater than 900 g/mol, preferably greater than 1000 g/mol, preferably greater than 1300 g/mol, and preferably greater than 2000 g/mol, and preferably les than 1,000,000 g/mol, preferably less than 500,000 g/mol, preferably less than 100,000 g/molm, preferably less than 50,000 g/mol, and preferably less than 25,000 g/mol, including all ranges and subranges therebetween such as, for example, 1,000 to 5,000 g/mol, 750 to 10,000 g/mol, etc.

Specific examples of suitable non-volatile hydrocarbon oils include, but are not limited to, liquid paraffin, liquid petroleum jelly, naphthalene oil, polybutylenes such as Indopol H-100 (molar mass or MW=965 g/mol), Indopol H-300 (MW=1340 g/mol) and Indopol H-1500 (MW=2160 g/mol) sold or manufactured by the company Amoco, polyisobutylenes, hydrogenated polyisobutylenes such as Parleam® or Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), decene/butene copolymers, polybutene/polyisobutene copolymers, especially Indopol L-14, polydecenes and hydrogenated polydecenes such as Puresyn 10 (MW=723 g/mol) and Puresyn 150 (MW=9200 g/mol) sold or manufactured by the company Mobil Chemicals, and mixtures thereof.

Preferably, the non-volatile hydrocarbon oil having a molecular weight greater than 400 g/mol is a "C3-C5 polyalkene" which includes all isomers of the relevant compounds. So, for example, "C4 polyalkene" includes polybutene and polyisobutene. It is to be further understood that the phrase "C3-C5 polyalkene" includes hydrogenated compounds and non-hydrogenated compounds.

Suitable examples of commercially-available C3-C5 polyalkenes include those sold under the Indopol® (non-hydrogenated compounds) and Panalane® (hydrogenated compounds) names by Ineos as noted above.

Preferably, hydrogenated C3-C5 polyalkenes have a molecular weight of 500 g/mol to 1500 g/mol, preferably from 600 g/mol to 1400 g/mol, and preferably from 750 g/mol to 1300 g/mol, including all ranges and subranges therebetween.

Preferably, non-hydrogenated C3-C5 polyalkenes have a molecular weight of 750 g/mol to 7500 g/mol, preferably from 900 g/mol to 6000 g/mol, and preferably from 1300 g/mol to 2500 g/mol, including all ranges and subranges therebetween.

Preferably, the non-volatile hydrocarbon oil having a molecular weight greater than 400 g/mol is present in the satin lip compositions of the present invention in amounts ranging from about 1% to about 30%, preferably from about 3% to about 25% and preferably from about 5% to about 15%, by weight, based on the total weight of the composition, including all ranges and subranges in between.

Additional Ingredients

Volatile Silicone Solvent

The volatile silicone solvent, if present, may be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 cSt) from Dow Corning | 102 | 3 |

The at least one volatile silicone solvent, if present, is generally present in the compositions of the present invention in an amount ranging from about 1% to about 15% by weight; preferably from about 2% to about 12% by weight; and preferably from about 3% to about 7% by weight, including all ranges and subranges therebetween, all weights being based on the weight of the composition as a whole.

Non-volatile Silicone Solvent

The satin lip compositions of the present invention may optionally further comprise at least one non-volatile solvent.

Non-volatile oils include low viscosity oils (having a viscosity from about 5 to about 10 centipoise) and high viscosity oils (having a viscosity of from about 100 to about 10,000 centipoise), and mixtures thereof. In contrast to waxes, oils are liquids at room temperature.

Non-limiting examples of suitable non-volatile silicone oils include polymethylsiloxanes (PDMS) with a linear or cyclic silicone chain, which are liquid or pasty at room temperature, especially cyclopolydimethylsiloxanes (cyclomethicones) such as cyclohexasiloxane; polydimethylsiloxanes (CTFA designation "dimethicones") comprising alkyl or alkoxy groups, which are pendent or at the end of a silicone chain, these groups containing from 2 to 24 carbon atoms; polydiethyl siloxanes; and dimethicone fluids having viscosity from about 300 cPs at 25° C. to about 1500 cPs at 25° C. Particularly useful dimethicone fluids have viscosity from about 350 cPs at 25° C. to about 1000 cPs at 25° C.

Specific examples of suitable for this invention high viscosity silicone oils include, but are not limited to, Xiameter® silicone fluids from Dow Corning.

The at least one non-volatile silicone oil, if present, is preferably present in the compositions of the present invention in an amount ranging from about 1% to about 15% by weight, preferably from about 2% to about 12% by weight, and preferably from about 3% to about 10% by weight, based on the total weight of the composition, including all ranges and subranges within these ranges.

However, according to particularly preferred embodiments of the present invention, the satin lip compositions are free of, substantially free of or devoid of silicone oils (volatile and non-volatile).

Also, according to particularly preferred embodiments of the present invention, the satin lip compositions are free of, substantially free of or devoid of silicone gums.

Also, according to particularly preferred embodiments of the present invention, the satin lip compositions are free of, substantially free of or devoid of both silicone oils (volatile and non-volatile) and silicone gums.

Also, according to particularly preferred embodiments of the present invention, the satin lip compositions include a satin-imparting component consisting essentially of hydrocarbon oil(s).

Colorants

The compositions of the present invention may optionally further comprise at least one colorant. Suitable colorants (coloring agents) include any colorant typically found in lip compositions. Suitable colorants include, but are not limited to, lipophilic dyes, pigments and pearlescent agents, and their mixtures.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

In accordance with preferred embodiments of lip compositions of the present invention, the colorant is preferably present in an amount sufficient to provide color to the lips, preferably in an amount of from about 0.1% to about 20% by weight, preferably from about 0.25% to about 15% by weight, and preferably from about 0.5 to about 10% by weight, of the total weight of the composition, including all ranges and subranges therebetween.

Auxiliaries/Additives

The compositions discussed above may additionally comprise an additive or auxiliary commonly used in cosmetic compositions and known to a person skilled in the art as being capable of being incorporated into a lip composition. Such additives or auxiliaries may be chosen from water or other solvents, thickeners, coalescents, preservatives, fragrances, surfactants, antioxidants, wetting agents, dispersing agents, antifoaming agents, neutralizing agents, stabilizing agents, active principles, UV screening agents, moisturizing agents, vitamins, proteins, ceramides, plant extracts, fibers, and the like, and their mixtures.

A person skilled in the art will take care to select the optional additional additives and/or the amount thereof such that the advantageous properties of the compositions according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the compositions of the invention should be cosmetically or dermatologically acceptable, i.e., they should contain a non-toxic physiologically acceptable. The compositions may be in any galenic form normally employed in the cosmetic and dermatological fields which is suitable for topical administration onto nails.

According to preferred embodiments of the present invention, methods of making a satin lip composition comprising combining about 10% to about 40% by weight of at least one silicone resin comprising at least one T unit, about 5% to about 40% by weight of at least one silicone acrylate copolymer, about 1% to about 15% by weight of at least one silicone wax, about 1% to about 15% by weight of at least one volatile hydrocarbon oil, and about 1% to about 30% at least one non-volatile hydrocarbon oil, all weights being based on the total weight of the composition, during preparation of the composition to form a satin lip composition are provided. Preferably, at least one colorant is also added during preparation of the composition.

According to preferred embodiments of the present invention, methods of making up and/or protecting lips comprising applying to the lips a satin lip composition of the present invention.

"Making up" as used herein means to provide decoration (for example, color) to the lips. "Protecting" as used herein means to inhibit damage to the lips such as, for example, sun damage.

In accordance with preferred embodiments of the preceding methods, at least one composition of the present invention is applied topically to the lips of a person in need of (desirous) the desired making up or protection in an amount sufficient to achieve the desired result. The compositions may be applied to the desired area as needed.

The compositions according to the invention can be manufactured by known processes used generally in the cosmetics or dermatological field.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

The present invention will be better understood from the examples which follow. The examples are intended to be nonrestrictive and explanatory only, with the scope of the invention defined by the claims.

Example 1

Evaluation Techniques

Compositions were evaluated for finish (shine), transfer-resistance, tack, and flake, according to the following procedures:

Shine (in vitro)

Films of compositions were deposited onto BLACK SCRUB PANEL P121-10N using a 1 MIL drawdown bar and an Automatic Drawdown Machine. The films were dried at room temperature (25° C.) for 5 minutes and analyzed using a gloss meter (BYK: micro-TRI-gloss) at an angle of 60°. Values below 20.0 correlate to matte finish on the lips and values above 60 correlate to glossy finish.

Transfer-Resistance (in vivo)

Compositions were applied on lips and allowed to dry for 15 minutes, and then the back of the hand was kissed. Color transfer was quantified as 0 (no transfer), 1 (trace), 2 (low transfer), 3 (medium transfer), 4 (high transfer).

Transfer-Resistance (in vitro)

Films of compositions were deposited onto BLACK SCRUB PANEL P121-10N using a 1 MIL drawdown bar. Films were allowed to dry 30 minutes at room temperature (25° C.), then a KimWipe (folded 3 times) was placed on top of the sample followed by 241 g weight for 15 seconds. Color transfer was quantified as 0 (no transfer), 1 (trace), 2 (low transfer), 3 (medium transfer), 4 (high transfer).

Tack (in vivo)

Compositions were applied on lips and allowed to dry for 15 minutes, and then the back of the hand was kissed. Tack was rated as 0 (no tack), 1 (low tack), 2 (medium tack), 3 (high tack).

Tack (in vitro)

Films of compositions were deposited onto contrast cards using a 3 MIL drawdown bar and an Automatic Drawdown Machine. The films were dried at room temperature (25° C.) overnight and analyzed using a Texture Analyzer equipped with a ball probe. Tack was measured after applying 350 g of force for 10 seconds. Then, the values of the tackiness were correlated to the comfort of wear of the tested products. The samples having tackiness of values higher than 100 gr/force were considered to be uncomfortable to wear. Tack values between 50-100 gr/force indicated medium comfort, and tack values of less than 50 gr/force were considered to be comfortable.

Flake (in vitro)

Compositions were tested for their flake-resistant properties. Samples were deposited onto Thera-Band® intermediate resistance exercise band (7×5 cm) surface using a 3 MIL drawdown bar. The samples were allowed to dry for 4 hours at room temperature (25° C.). The samples were weighed and stretched to total 30 cm. The stretching was repeated ten times for each sample and weighed again to note any product lost. Flaking of the dry samples is correlated to the durability of wear. Flake was calculated using the following equation: [(weight in grams after 10 stretches)/(initial weight in grams)]×100. The higher the flake value, the less durable the wear.

Example 2

Composition Preparation

Compositions were prepared by the following procedure:

The mixture of pigment and film formers was processed to create pigment dispersion. The blend was processed using Disconti Mill until the dispersion passed the Hegman Gauge test (ASTM D1210-05). Then, the pigment dispersion and the remaining ingredients were combined stirring at 70° C. until a homogeneous liquid composition was obtained. After that, the composition was cooled down to the room temperature and transferred to desired containers and/or applicators.

Example 3

Comparative Testing

Invention Compositions

|  | Inv. 1 | Inv. 2 | Inv. 3 | Inv. 4 | Inv. 5 | Inv. 6 |
| --- | --- | --- | --- | --- | --- | --- |
| Pigment grind |  |  |  |  |  |  |
| POLYPROPYLSILSESQUIOXANE (and) ISODODECANE (72% active) | 49.21 | 49.21 | 49.21 | 49.21 | 49.21 | 49.21 |
| ACRYLATES/DIMETHICONE COPOLYMER (40% active) | 41.27 | 41.27 | 41.27 | 41.27 | 41.27 | 41.27 |
| Pigments | 9.52 | 9.52 | 9.52 | 9.52 | 9.52 | 9.52 |
| Full formula |  |  |  |  |  |  |
| Pigment grind | 63 | 63 | 63 | 63 | 63 | 63 |
| HYDROGENATED POLYISOBUTENE | 5 | 5 | 5 | 10 | 0 | 5 |
| SQUALANE | 10 | 10 | 10 | 7.5 | 15 | 5 |
| POLYISOBUTENE | 5 | 5 | 0 | 0 | 0 | 5 |
| MAGNESIUM STEARATE | 5 | 5 | 4 | 5 | 15 | 5 |
| C30-45 ALKYLDIMETHYLSILYL POLYPROPYLSILSESQUIOXANE | 7 | 5 | 8 | 7 | 2 | 0 |
| ISODODECANE | QS | QS | QS | QS | QS | QS |
| Evaluation |  |  |  |  |  |  |
| Shine (in vitro) | 29.2 | 57.7 | 31.4 | 31.2 | 21.3 | 27.7 |
| Shine STDEV | 1.7 | 1.6 | 2.9 | 3.5 | 1.7 | 5.2 |
| Transfer 1 (in vivo) | 1 | 1 | 1 | 1 | 2 | 1 |
| Transfer 2 (in vitro) | 1 | 1 | 1 | 1 | 1 | 0 |
| Tack 1 (in vivo) | 1 | 0 | 1 | 0 | 0 | 2 |
| Tack 2 (in vitro) | 76.6 | 39.1 | 64.2 | 76.7 | 12.1 | 8.3 |
| Tack 2 STDEV | 8.6 | 8.0 | 9.2 | 9.4 | 4.3 | 3.5 |
| Flake (in vitro) | 0 | 0 | 0 | 0 | 3 | 0 |

Comparative Compositions

|  | Comp. 1 | Comp. 2 | Comp. 3 | Comp. 4 | Comp. 5 | Comp. 6 |
|---|---|---|---|---|---|---|
| Pigment grind |  |  |  |  |  |  |
| POLYPROPYLSILSESQUIOXANE (and) ISODODECANE (72% active) | 49.21 | 49.21 | 49.21 |  |  |  |
| ACRYLATES/DIMETHICONE COPOLYMER (40% active) | 41.27 | 41.27 | 41.27 |  |  |  |
| Pigments | 9.52 | 9.52 | 9.52 |  |  |  |
| Full formula |  |  |  |  |  |  |
| Pigment grind | 63 | 63 | 63 |  |  |  |
| HYDROGENATED POLYISOBUTENE | 5 | 5 | 5 |  |  |  |
| SQUALANE | 10 | 10 | 10 |  |  |  |
| POLYISOBUTENE | 0 | 0 | 0 |  |  |  |
| MAGNESIUM STEARATE | 10 | 14 | 4 |  |  |  |
| C30-45 ALKYLDIMETHYLSILYL POLYPROPYLSILSESQUIOXANE | 4 | 8 | 15 |  |  |  |
| ISODODECANE | QS | QS | QS |  |  |  |
| Evaluation |  |  |  |  |  |  |
| Shine | 14.9 | 6.3 | 12.8 | 9.3 | 26.9 | 5.7 |
| Shine STDEV | 0.5 | 0.1 | 0.2 | 1.4 | 2 | 0.1 |
| Transfer 1 (in vivo) | 0 | 0 | 3 | 0 | 3 | 0 |
| Transfer 2 (in vitro) | 1 | 1 | 1 | 0 | 3 | 0 |
| Tack 1 (in vivo) | 1 | 2 | 3 | 1 | 1 | 3 |
| Tack 2 (in vitro) | 78.5 | 165.6 | 117.8 | 4.5 | 37.9 | 108.2 |
| Tack 2 STDEV | 11.8 | 5.5 | 15.3 | 1.0 | 10.4 | 7.6 |
| Flake (in vitro) | 0 | 0 | 0 | 0 | 3 | 0 |

*Comparative 4
DIMETHICONE, TRIMETHYLSILOXYSILICATE, ISODODECANE, NYLON-611/DIMETHICONE COPOLYMER, DIMETHICONE CROSSPOLYMER, C30-45 ALKYLDIMETHYLSILYL POLYPROPYLSILSESQUIOXANE, LAUROYL LYSINE, ALUMINA SILICA SILYLATE, DISODIUM STEAROYL GLUTAMATE, PHENOXYETHANOL, CAPRYLYL GLYCOL, LIMONENE, ALUMINUM HYDROXIDE, PARAFFIN, BENZYL BENZOATE, BENZYL ALCOHOL, CITRONELLOL PARFUM/FRAGRANCE, Pigments

**Comparative 5
Isododecane, Diisostearyl Malate, Hydrogenated Polyisobutene, C10-18 Triglycerides, Dimethicone Crosspolymer, Oryza Sativa (Rice) Bran Wax, Pentylene Glycol, Silica Silylate, Polyethylene, Disteardimonium Hectorite, Triethoxycaprylylsilane, Propylene Carbonate, Pigments

***Comparative 6
ISODODECANE, TRIMETHYLSILOXYSILICATE, NYLON-611/DIMETHICONE COPOLYMER, DISTEARDIMONIUM HECTORITE, LAUROYL LYSINE, C30-45 ALKYLDIMETHYLSILYL POLYPROPYLSILSESQUIOXANE, ALUMINA, PROPYLENE CARBONATE, SYNTHETIC FLUORPHLOGOPITE, SILICA, CALCIUM SODIUM BOROSILICATE, CALCIUM ALUMINUM BOROSILICATE, POLYETHYLENE TEREPHTHALATE, PARFUM/FRAGRANCE, ALUMINUM HYDROXIDE, ACRYLATES COPOLYMER, BENZYL ALCOHOL, DIMETHICONE, PARAFFIN, TIN OXIDE, Pigments

What is claimed is:

1. A satin lip composition comprising at least one silicone resin comprising at least one T unit, at least one silicone acrylate copolymer, at least one silicone wax, at least one volatile hydrocarbon oil, wherein the at least one volatile hydrocarbon oil is present in an amount less than or equal to 25% by weight based on the total weight of the composition, and at least one non-volatile hydrocarbon oil having a molecular weight greater than 400 g/mol which is a C3-C5 polyalkene, wherein the composition has average gloss properties, measured at 60°, of 20 to 60 and wherein the silicone resin(s) comprising at least one T unit and silicone acrylate copolymer(s) are present in a weight ratio of from about 5:1 to about 1.5:1.

2. The satin lip composition of claim 1, wherein the composition comprises about 10% to about 40% by weight of at least one silicone resin comprising at least one T unit, about 5% to about 40% by weight of at least one silicone acrylate copolymer, about 1% to about 15% by weight of at least one silicone wax, about 1% to less than or equal to 25% by weight of at least one volatile hydrocarbon oil, and about 1% to about 30% at least one non-volatile hydrocarbon oil having a molecular weight greater than 400 g/mol, all weights being based on the total weight of the composition.

3. The satin lip composition of claim 1, wherein the composition is anhydrous.

4. The satin lip composition of claim 1, wherein the silicone resin(s) comprising at least one T unit and silicone acrylate copolymer(s) are present in a weight ratio of from about 4:1 to about 1.5:1.

5. The satin lip composition of claim 1, wherein the silicone resin(s) comprising at least one T unit and silicone acrylate copolymer(s) are present in a weight ratio of from about 3:1 to about 1.5:1.

6. The satin lip composition of claim 1, wherein the at least one silicone acrylate copolymer and the at least one silicone resin comprising at least one T unit are present in a combined amount ranging from about 25% to about 70% by weight based on the total weight of the composition.

7. The satin lip composition of claim 1, wherein the non-volatile hydrocarbon oil is polyisobutene, hydrogenated polyisobutene, or a mixture thereof.

8. The satin lip composition of claim 1, wherein the silicone wax is C30-45alkyldimethylsilyl polypropylsilsesquioxane.

9. The satin lip composition of claim 1, further comprising magnesium stearate.

10. The satin lip composition of claim 1, further comprising at least one colorant.

11. The satin lip composition of claim 1, wherein the composition is devoid of silicone gum.

12. The satin lip composition of claim 1, wherein the composition is devoid of silicone oil.

13. The satin lip composition of claim 1, wherein the composition is devoid of both silicone gum and silicone oil.

14. The satin lip composition of claim 1, wherein the composition comprises a satin-imparting component consisting essentially of hydrocarbon oil(s).

15. A method of making up lips comprising applying the composition of claim 1 to the lips.

16. An anhydrous satin lip composition comprising:
    about 10% to about 40% by weight of at least one polypropylsilsesquioxane,
    about 8% to about 20% by weight of at least one acrylates/dimethicone copolymer,
    about 2% to about 10% by weight of at least one C30-45 alkyldimethylsilyl polypropylsilsesquioxane,
    about 5% to about 20% by weight of at least one volatile hydrocarbon oil, and
    about 5% to about 15% by weight of at least one non-volatile hydrocarbon oil having a molecular weight greater than 400 g/mol which is a C3-C5 polyalkene, all weights being based on the total weight of the composition,
    wherein the composition has average gloss properties, measured at 60°, of 20 to 60 and wherein the silicone resin(s) comprising at least one T unit and silicone acrylate copolymer(s) are present in a weight ratio of from about 5:1 to about 1.5:1.

17. The satin lip composition of claim 16, wherein the non-volatile hydrocarbon oil is polyisobutene, hydrogenated polyisobutene, or a mixture thereof.

18. The satin lip composition of claim 17, wherein the silicone resin(s) comprising at least one T unit and silicone acrylate copolymer(s) are present in a weight ratio of from about 3:1 to about 1.5:1.

19. The satin lip composition of claim 1, wherein the at least one volatile hydrocarbon oil is present in an amount of less than about 20% by weight based on the total weight of the composition.

20. The satin lip composition of claim 1, wherein the at least one volatile hydrocarbon oil is present in an amount of from about 5% to about 20% by weight based on the total weight of the composition.

* * * * *